United States Patent
Stewart (10) Patent No.: US 11,867,161 B2
(45) Date of Patent: Jan. 9, 2024

(54) OIL MONITORING

(71) Applicant: SPM Oil & Gas Inc., Fort Worth, TX (US)

(72) Inventor: Trever Dean Stewart, Fort Worth, TX (US)

(73) Assignee: SPM Oil & Gas Inc., Fort Worth, TX (US)

(*) Notice: Subject to any disclaimer, the term of this patent is extended or adjusted under 35 U.S.C. 154(b) by 676 days.

(21) Appl. No.: 17/044,313

(22) PCT Filed: Apr. 1, 2019

(86) PCT No.: PCT/US2019/025245
§ 371 (c)(1),
(2) Date: Sep. 30, 2020

(87) PCT Pub. No.: WO2019/195198
PCT Pub. Date: Oct. 10, 2019

(65) Prior Publication Data
US 2021/0018001 A1 Jan. 21, 2021

Related U.S. Application Data

(60) Provisional application No. 62/651,195, filed on Apr. 1, 2018.

(51) Int. Cl.
*F04B 1/00* (2020.01)
*F04B 53/18* (2006.01)
(Continued)

(52) U.S. Cl.
CPC .............. *F04B 1/00* (2013.01); *F04B 53/18* (2013.01); *F04D 15/0088* (2013.01); *G01N 15/0656* (2013.01); *G01N 33/2888* (2013.01)

(58) Field of Classification Search
CPC ........ F04B 1/00; F04B 53/18; F04B 2207/70; F04D 15/0088; F04D 29/061;
(Continued)

(56) References Cited

U.S. PATENT DOCUMENTS

| | | | | |
|---|---|---|---|---|
| 5,005,409 A | * | 4/1991 | Hochstein | G01F 23/268 |
| | | | | 73/304 C |
| 6,443,006 B1 | * | 9/2002 | Degrave | G01F 23/266 |
| | | | | 73/304 C |

(Continued)

FOREIGN PATENT DOCUMENTS

| WO | 2017044821 A1 | 3/2017 |
|---|---|---|
| WO | 2019046680 A1 | 3/2019 |

OTHER PUBLICATIONS

International Search Report and Written Opinion received in Patent Cooperation Treaty Application No. PCT/US2019/025245, dated Jun. 14, 2019.

*Primary Examiner* — Akm Zakaria (57) ABSTRACT

The oil quality in an oil reservoir of a pump is monitored using the disclosed oil-monitoring sensor. The oil-monitoring sensor includes a first capacitive portion for measuring oil level and a second capacitive portion for measuring dielectric constant of the oil. Changes in dielectric constant of the oil are indicative of degradation of the quality of the oil (e.g., due to contaminants, oxidation, etc.) So oil-monitoring sensor is used to indicate various parameters about the oil quality to an operator. Using the disclosed sensors, the quality of the lubricant and/or cooling oil used by the pump may be monitored without needing to be present at the pump, or without needing to access the interior of the pump (or oil reservoir).

18 Claims, 8 Drawing Sheets

(51) Int. Cl.
 *F04D 15/00* (2006.01)
 *G01N 15/06* (2006.01)
 *G01N 33/28* (2006.01)

(58) Field of Classification Search
 CPC .......... G01N 15/0656; G01N 33/2888; G01N 2015/0053; F02D 2200/023; F02D 41/22; F16N 2200/00; F16N 2250/08; F16N 2250/18; F16N 2250/30; F16N 29/00; F01M 11/12; F05D 2270/80
 See application file for complete search history.

(56) References Cited

U.S. PATENT DOCUMENTS

| | | | |
|---|---|---|---|
| 8,833,328 B2* | 9/2014 | Palazzolo | F01M 11/03 384/429 |
| 2003/0222656 A1* | 12/2003 | Phillips | G01N 27/02 324/605 |
| 2004/0108859 A1* | 6/2004 | Nicholson | G01N 27/02 324/633 |
| 2006/0288877 A1* | 12/2006 | Chambon | A47J 37/1266 99/342 |
| 2010/0174496 A1* | 7/2010 | Adnan | G01M 3/24 702/34 |
| 2016/0177945 A1* | 6/2016 | Byrne | F04B 53/18 184/6 |
| 2016/0356270 A1* | 12/2016 | Zhang | F04B 51/00 |
| 2018/0158261 A1* | 6/2018 | Ottikkutti | G01N 33/2888 |

* cited by examiner

OIL MONITORING

RELATED APPLICATION

This application is a national phase application of Patent Cooperation Treaty Application No. PCT/US2019/025245 filed Apr. 1, 2019, which claims priority to and the benefit of U.S. Provisional Application No. 62/651,195 filed Apr. 1, 2018, which is incorporated herein by reference in its entirety.

TECHNICAL FIELD

This disclosure relates to a system and method for monitoring oil, e.g., used for lubricant of machinery, such as pumps.

BACKGROUND

Industrial equipment in the oil and gas and mining industries require lubricants to function properly. Typically, some type of oil, hydraulic, or other lubricant is used to keep various pumps and industrial equipment properly lubricated. Over time, oil used for lubrication degrades due to oxidation, thermal breakdown, contamination, etc. In turn, this can reduce the ability of the oil to perform its lubricating (or other) function, resulting in wear of components or loss of performance of the equipment being lubricated. The can be particularly impactful to oil-and-gas and mining operations, which use industrial pumps that must be properly lubricated to function. If lubrication fails, the pumps may be damaged or have to be taken offline, causing expensive delays in extraction and mining.

Oil needs to be replaced in industrial equipment before the oil itself degrades, but that is not always the case. Conventionally, oil is replaced based on a pre-set schedule or run life of a piece of equipment. For example, oil may be replaced after so many hours of operation or after a certain number of days. More complex methods require maintenance personnel to inspect the oil (either visually or with testing equipment) and determine whether it is degraded beyond a certain point that could impact its equipment. Replacing or inspecting at predetermined schedules does not always lead to the best utilization of the oil.

SUMMARY

The following summary is provided to illustrate some examples disclosed herein. It is not meant, however, to limit all examples to any particular configuration or sequence of operations.

Some examples disclosed herein generally relate to a system for monitoring the oil quality of a pump. The system includes an oil reservoir in fluid connection with the pump and a sensor. The sensor comprises a first capacitive portion for measuring oil level and a second capacitive portion for measuring dielectric constant of the oil. Changes in dielectric constant of oil can be indicative of degradation of the quality of the oil (e.g., due to contaminants, oxidation, etc.) Thus, an operator using the system may be able to determine the oil quality of e.g., lubricant and/or cooling oil used by the pump without needing to be present at the pump, or without needing to access the interior of the pump (or oil reservoir). For example, signals from the sensor may be received by an external processor (via a wireless or wired network), which may determine whether there is an issue with the oil being measured.

In one embodiment the first capacitive portion is arranged in the reservoir so as to remain substantially fully immersed in the oil during operation of the pump. This may ensure that the oil level measurement of the first capacitive portion is constant. This may limit function of the sensor to oil quality measurements and may simplify the data produced by the sensor.

In one embodiment the first and second capacitive portions may each comprise a first capacitive element and share a common second capacitive element spaced from the respective first capacitive elements. The shared nature of the second capacitive element may mean that the measurement of dielectric constant is affected by the measurement of oil level. Where oil level is not a concern, the immersion of the first capacitive element may reduce or eliminate this effect.

In one embodiment the second capacitive element may be tubular, and each first capacitive element may be arranged concentrically within the second capacitive element.

In one embodiment the first capacitive elements may be electrically insulated from one another.

In one embodiment the sensor may further comprise a temperature sensing portion for sensing the temperature of the oil. The dielectric constant of an oil can be affected by the temperature of the oil. Hence, in addition to degradation of the oil, a change in temperature can cause the dielectric constant of the oil to change. The system may further comprise a processor. The processor may be adapted to adjust the sensed dielectric constant based on the sensed temperature of the oil. That is, the processor (e.g., in the form of a processing circuit) may compensate changes in the measured dielectric constant based on changes in the temperature of the oil in order to remove the effect of the temperature changes from the measurements. In this way, the measurements are solely indicative of changes in the quality of the oil.

In one embodiment the oil reservoir may be fluidly connected to a power end sump of the pump. This connection may be way of hoses, pipes, etc. Alternatively, the oil reservoir may be in the form of cartridge located in or adjacent to a sump of the pump. The cartridge may be removably mounted within the sump such that the sensor may be accessed for maintenance, replacement, etc. The cartridge may comprise a receptacle portion to retain a portion of the oil in the sump at a level that is sufficient to ensure that at least the first capacitive element is immersed in the oil.

In one embodiment the oil reservoir may be configured to maintain an oil level in the oil reservoir that is sufficient to substantially immerse the sensor in the oil during operation of the pump. Again, this may ensure that the oil level measurement of the sensor remains constant and does not affect the measurements of oil quality.

In one embodiment the sensor may be an automotive sensor. Automotive sensors, while not immediately suited to use with pumps, may provide a simple and cost effective alternative to more complex pump sensors. Automotive application of such sensors differs significantly to the present application in an oil and gas pump (e.g., a hydraulic fracturing or "frac" pump) For example, in vehicles the oil sump is generally located in the engine. In frac pumps, oil is used for cooling (as well as lubricant) and, as such, the power end does not comprise a sump—instead there is continual drainage to an external cooling system. Oil in frac pumps also generally experiences much higher flow rates and pressures. As a result of this, oil levels in frac pumps fluctuate to an extent where measuring the oil level may not be particularly feasible or valuable to an operator. This is different to automotive applications, where a reduction in oil level may be slow and consistent, and where such measurement of oil level may be valuable to an operator to ensure that oil is replenished at an appropriate time.

In one embodiment the pump may be a positive displacement pump. The pump may, for example, be a frac pump.

Also disclosed is a method of determining the quality of oil in the reservoir of a pump. The method comprises providing a sensor capable of sensing the dielectric constant of oil and oil level based on the degree of exposure of the sensor to the oil. The method further comprises exposing the sensor to a substantially constant oil level, and determining quality of the oil based on the sensed dielectric constant of the oil. As is the case with some sensor types, changes in oil level measurement can affect oil quality (e.g., dielectric constant) measurements. Where this is the case, ensuring that the oil level measurements remains constant can eliminate any effects such measurements have on the determination of oil quality.

In one embodiment the method may further comprise the step of fully immersing an oil level sensing portion of the sensor in the oil. This may help to ensure a constant oil level measurement.

In one embodiment the method may further comprise sensing the temperature of the oil. The sensed dielectric constant may be adjusted based on the sensed oil temperature in order to determine the quality of the oil. As set forth above, changes in oil temperature can have an effect on dielectric constant of oil. Hence, in order to ensure that changes in dielectric constant are solely indicative of changes in oil quality, the dielectric constant may be adjusted based on the temperature of the oil.

Also disclosed is a method of retrofitting a frac pump with an oil quality detection system. The method comprises mounting a sensor in an oil reservoir of the frac pump. The sensor comprises a first capacitive portion for measuring oil level, and a second capacitive portion for measuring dielectric constant of the oil.

In one embodiment the method may further comprise fluidly connecting an external reservoir to the frac pump. The sensor may be mounted in the external reservoir.

In one embodiment the method comprises mounting the sensor in the oil reservoir such that the first capacitive portion remains immersed in oil in the oil reservoir during operation of the pump.

BRIEF DESCRIPTION OF THE DRAWINGS

The disclosed examples are described in detail below with reference to the accompanying drawing figures listed below.

DETAILED DESCRIPTION

In the following disclosure, reference is made to accompanying drawings that form a part of the detailed description. The illustrative embodiments and examples described herein and depicted in the accompanying drawings are not intended to be limiting. Other embodiments may be additionally or alternatively used—and different configurations and/or components used—without departing from the spirit or scope of the subject matter presented. It will be readily understood that the aspects of the present disclosure, as generally described herein and illustrated in the drawings can be arranged, substituted, combined, separated and designed in a wide variety of different configurations, all of which are contemplated in this disclosure.

Figure 1A:
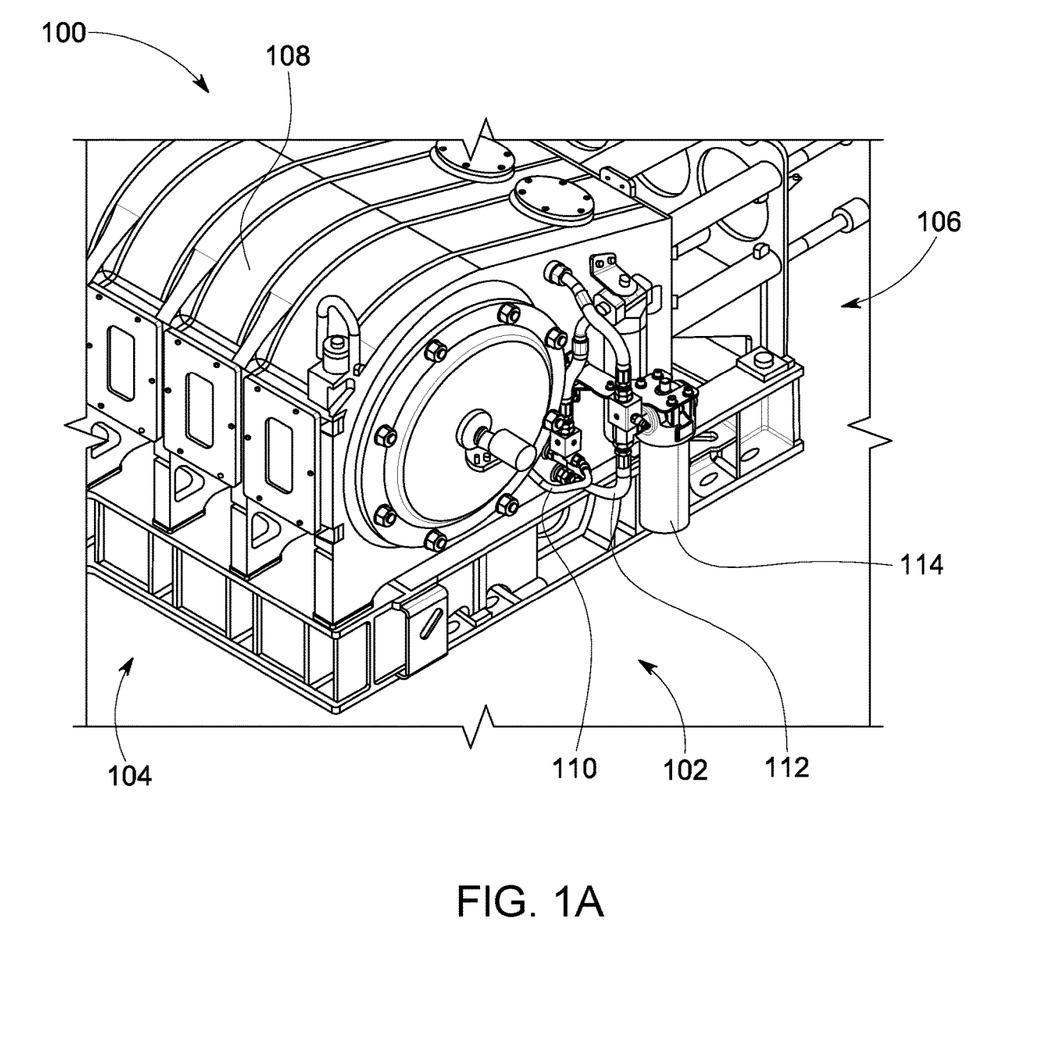
FIGS. 1A and 1B are respective perspective and detailed perspective views of a pump equipped with an oil sensor, according to some examples.
Figure 1B:
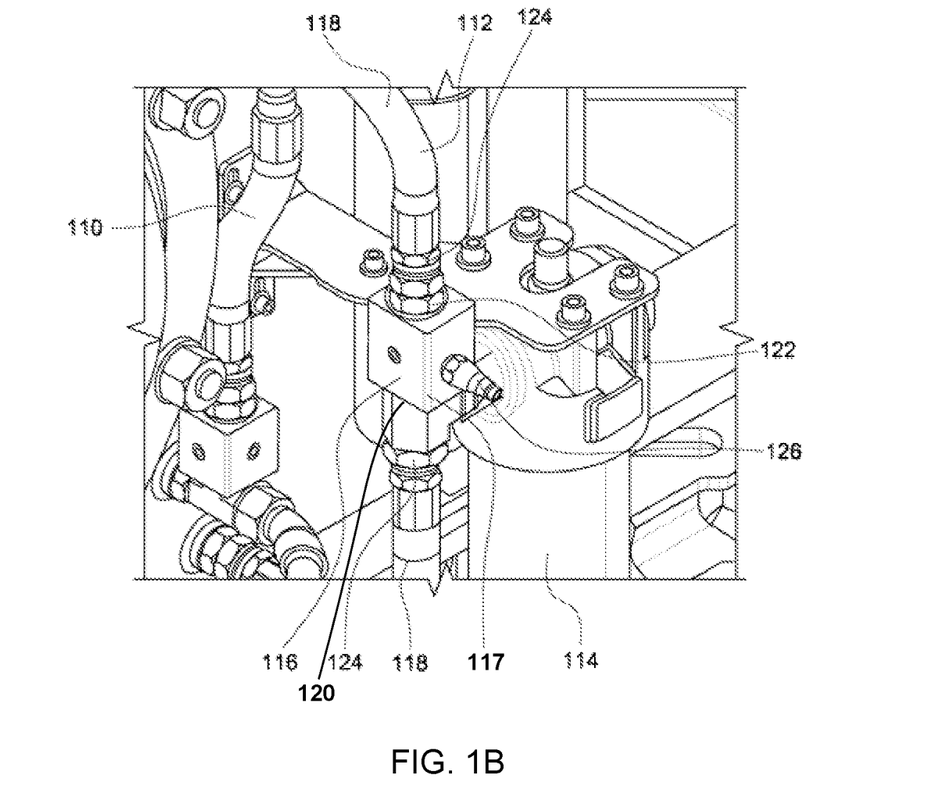

FIGS. 1A and 1B illustrate an environment 100 for a pump 102 equipped with an oil sensor for monitoring oil quality within the pump 102. In some embodiments, the pump 102 is a reciprocating pump having a power end 104 and a fluid end 106. This type of pump 102 may be used for e.g., hydraulic fracturing ("tracking"), cementing, or acidizing of a subterranean well. In general, such pumps are suitable for pumping fluid (or a slurry) at high pressures. The illustrated pump 102 may be mounted to a truck or a skid for transport to various sites.

In one embodiment, the fluid end 106 of the pump 102 includes five cylinders, each having a respective plunger bore and a plunger that reciprocates in the respective plunger bore. When rotated (e.g., by a motor) the plungers are driven so as to pump fluid at the fluid end of the pump 102.

The power end 104 includes a crankshaft housing 108 that houses a crankshaft, which may be driven by a motor (neither of which is apparent from the figure). Also included in the power end 104 is a lubricant system for lubricating various components of the power end 104 (e.g., crankshaft shell bearings, knuckle bearings, crosshead bearings, gears and roller bearings). Although not fully depicted, this may include one or more lubricant lines 110, 112 (or loops) that supply lubricant to the components that are located within the crankshaft housing 108. The illustrated embodiment includes two such lubricant lines 110, 112, although only one of these lines 112 will be described in more detail below. Additional lubrication lines may be used, e.g., 3-10.

The lubricant block 116 includes sidewalls 117 arranged to form a cube-like shape and which define an internal cavity including an inlet 120 and an outlet 122, thereby allowing oil to pass through the block 116. In some embodiments, the hoses 118 are connected to the inlet 120 and outlet 122 by way of respective releasable coupling arrangements 124. Alternatively, the hoses 118 may be connected to the inlet 120 and outlet 122 via latches, buttons, screws, welds, adhesives, or other types of fasteners.

Figure 1C:
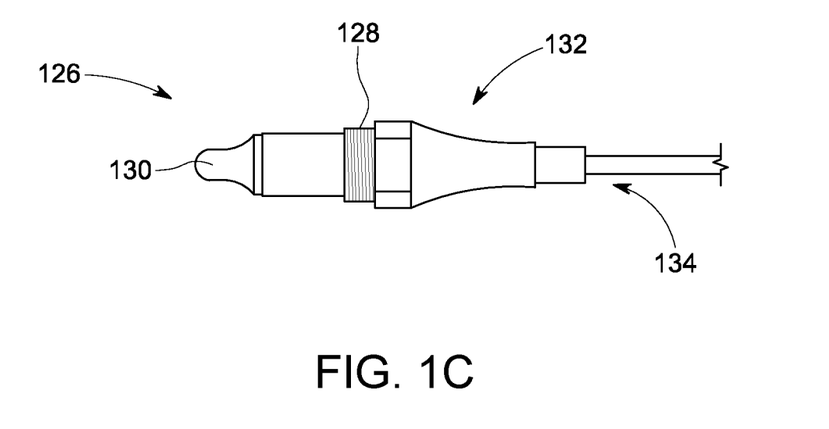
FIG. 1C is a side view of an oil sensor, according to some examples.

An oil sensor 126 is mounted (and sealed) in one of the sidewalls 117 of the lubricant block 116. While referred to herein as an "oil" sensor 126 to aid the reader, embodiments may use the disclosed sensor 126 to monitor and detect the quality of lubricants other than oil. The oil sensor 126, which is shown in more detail in FIG. 1C, is of the type that is capable of measuring the dielectric constant of a lubricant (e.g., oil). To facilitate mounting of the oil sensor 126 in the lubricant block 116, the sensor includes a threaded portion 128 that engages a corresponding threaded portion of the lubricant block. This non-permanent mounting allows the oil sensor 126 to be removed, for e.g., inspection, replacement, repair, etc. It also allows, in some embodiments, for the oil sensor 126 projecting into the cavity of the lubricant block 116 to be adjusted.

The oil sensor 126 includes an electrode 130 that, when mounted to the lubricant block 116, is exposed to oil within the cavity. When exposed in this way, the electrode 130 defines a capacitor with the lubricating oil (the dielectric) in its vicinity (e.g., referred to as an "oil/electrode capacitor"). The sensor 126 also includes a body 132 that (sealingly) houses a circuit which, in combination with the oil/electrode capacitor, forms a resonant circuit. This arrangement allows the sensor 126 to produce an electrical signal that indicates the dielectric constant of the oil flowing past the sensor electrode 130. This electrical signal may then be monitored for real-time determination of the quality of the oil being used to lubricate the pump, or other industrial equipment.

An end of the oil sensor 126 opposite the electrode 130 comprises a socket 134 that allows the sensor to be connected to a processor for processing of the signal. This processing is discussed below in further detail.

Figure 2:
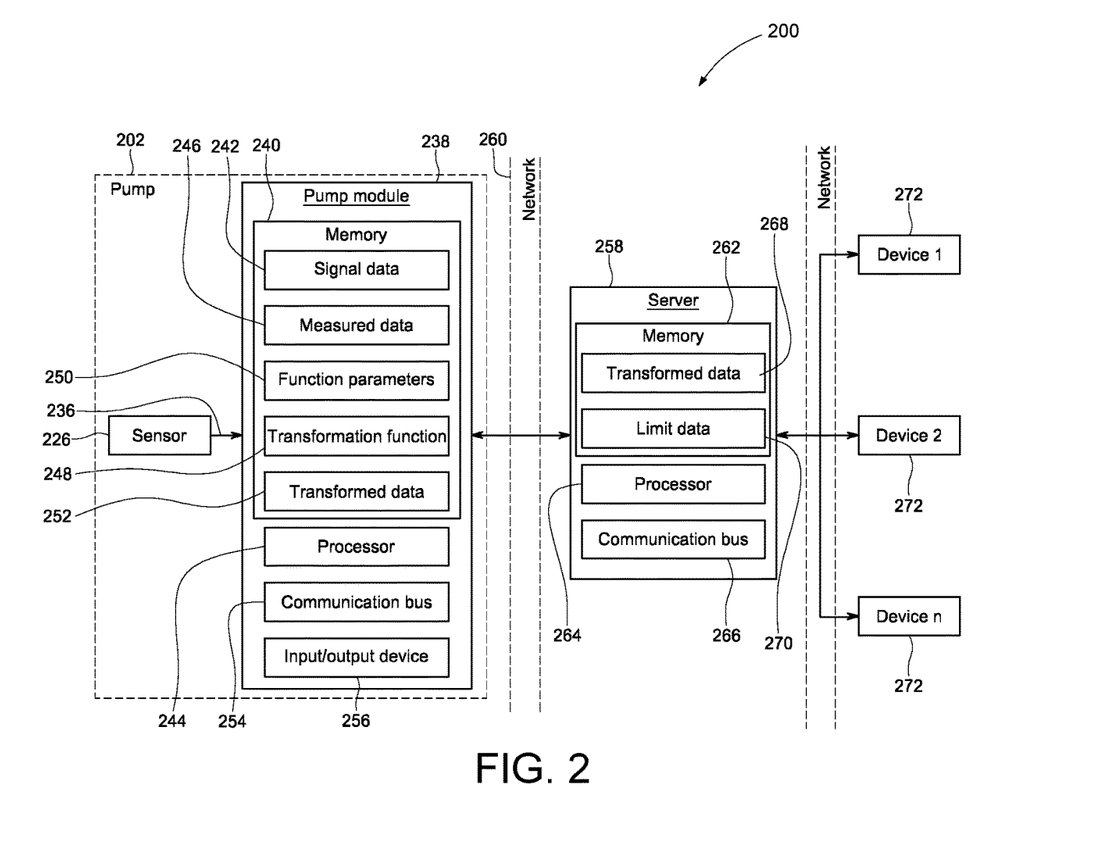
FIG. 2 is a block diagram of an environment for monitoring lubrication using an oil sensor, according to some examples.

FIG. 2 is a block diagram of an environment 200 for monitoring lubrication using the oil sensor 226, according to some examples. Oil sensor 226 may take the form of oil sensor 126 discussed above. In particular, environment 200 shows how the electrical signal from the oil sensor 226 is processed to determine the quality of the oil sensed by the sensor. The signal produced by the oil sensor 226 may, for example, be in the form of a waveform having a varying duty cycle, and the duty cycle may be indicative of the dielectric constant of oil in the lubrication block of the pump 202. The signal may be transmitted via a wired or wireless connection 236 with the oil sensor 226.

The system comprises pump module 238 that receives the signal from the oil sensor 226 (e.g., via the wireless or wired connection 234). The pump module 236 can be (physically) disposed on, or in proximity to, the pump 202. Alternatively, the pump module 238 may be located in a centralised control centre. The pump module 238 is configured to receive, and process, the signal from the oil sensor 226 in real-time. This processing includes converting the waveform, received from the sensor 226, into a value and then subsequently transforming that value.

The pump module 238 comprises a memory 240 that receives and stores, among other data, the signal 242 transmitted from the sensor 226. The memory 240 may comprise any known memory architecture and may include hard disk, integrated circuit ("IC") memory, read-only memory ("ROM"), programmable ROM ("PROM"), random access memory ("RAM"), flash memory, floppy disks, CD ROM, and any other type of memory.

The pump module 238 also comprises a processor 244, which may constitute one or more processing devices (e.g., integrated circuits (ICs}, processors, programmable logic device (PLD), systems on a chip (SoC), or the like). The processor 244 is configured to receive the signal data 242 from the memory 240, and determine measured values of the dielectric constant of the oil sensed by the oil sensor 226. In the present embodiment, the processor 244 determines this by analysing the signal data 242 and calculating the duty cycle of the signal data 242. As set forth above, the duty cycle is indicative of the dielectric constant of the oil sensed by the oil sensor 226. This measured value 246 is then stored in the memory 240 for further processing by the processor 244.

Although the dielectric constant of the oil can be determined directly from this raw duty cycle (measured) data 246, there are several reasons that an operator may wish to further process this data 246. For example, the pump module 238 may form part of a larger system of similar pump or machine modules that receive data from various other machines. The measured data 246 may need to be adjusted so as to fall within a particular range of values so as to be comparable, combinable or compatible with values received from other machines.

The processor 240 may, for example, pass the measured data 246 through a function (e.g., linear) to adjust the data to be within the particular range of values. The function 248 may be stored in the memory 240, and may include one or more parameters 250 that are also stored in the memory 240.

Another reason the measured data 246 may be further processed by the processor 238 is to compensate for various changes in the pump 202, and in the oil being sensed. For example, the dielectric constant of an oil may be affected by the temperature of the oil. Hence, in some cases (e.g., where there are significant temperature changes) the measured data 246 may need to be adjusted to compensate for changes in the temperature. Such a transformation of the data 246 may be performed, for example, by adjusting a parameter of the function 250 stored by the memory (and used by the processor 244). This may be done manually, or by way of input from a temperature sensor measuring the temperature of the oil in the pump (e.g., in proximity to the dielectric sensor).

Other than to compensate for temperature changes, the parameters 250 of the stored function 248 may be adjusted based on the type of oil used in the pump 202. Oil type may be varied based on operating conditions—for example, oil types may differ between seasons. In this respect, the pump module 238 may be calibrated for a particular oil type to ensure that there is consistency in the processed data 252 for all oil types. As will be discussed in more detail below, the configuration of the pump module 238 may allow calibration to occur (e.g., after an oil change) remotely. That is, it may not be necessary for an operator to be physically present at the pump module 238 in order to calibrate the pump module 238 when the oil is changed.

The pump module 238 further includes a communications bus 254 that facilitates the processing of the stored data in the memory 240 and by the processor 244, by enabling communication between the processor 244 and the memory 240.

The pump module 238 also includes an input/output (I/O) device 256, which comprises means allowing the pump module 238 to communicate with external components of the system (e.g., such as the sensor 226). The I/O device 256 also enables communication between the pump module 238 and an external server 258. In the illustrated embodiment, this communication is across a wireless (as opposed to a wired) network 260. More specifically, the I/O device 256 of the pump module 238 includes an antenna that enables communication on a mobile network and allows data to be transmitted from the pump module 238 to the external server 258. In other embodiments, the pump module 238 may be configured for communication on, for example, a secured wireless fidelity (WIFI) network or a network suitable for 'smart devices' (e.g., a low-power wide-area network (LPWAN)).

In some embodiments, the external server 258 is a cloud-based server and, like the pump module 238, includes memory 262, a processor 264, and a communication bus 266 for communication therebetween. In operation, the pump module 238 communicates the transformed data 252 to the external server 258, which stores these values in its respective memory 262. The processor 264 of the server 258 is configured to compare the received transformed data 268 (which is indicative of the dielectric constant of the oil) with a predetermined limit value 270. When the transformed data 268 received from the pump module 238 falls below the predetermined limit value 270, the processor 264 produces an alert. Because this value is indicative of the dielectric constant of the oil, and because the dielectric constant of the oil relates to the quality of the oil, such an alert may signify that the oil has fallen below an acceptable level.

This alert is transmitted to, and received by, one or more devices 272 wirelessly (e.g., through a wireless network) connected to the cloud-based external server. These devices 272 may include, for example, a desktop computer, a laptop computer, a mobile phone, a tablet, etc. An operator of one of these devices 272 may act on the alert by adjusting an operating parameter of the pump 202, or by replacing the oil in the pump 202.

Other than receiving alerts, the devices 272 may be provided with access to the server 258. This access may allow a device 272 to be used to adjust the limits 270 stored in the memory 262 of the server 258. Alternatively or additionally, a device 272 may be used to view current and/or historical values of the transformed data 268 stored in the memory 262 of the server 258. In other words, an operator may use device 272 to make an assessment of the quality of the oil used in the pump 22, and can also determine how oil quality in the pump 202 has changed over a particular time period.

Figure 3A:
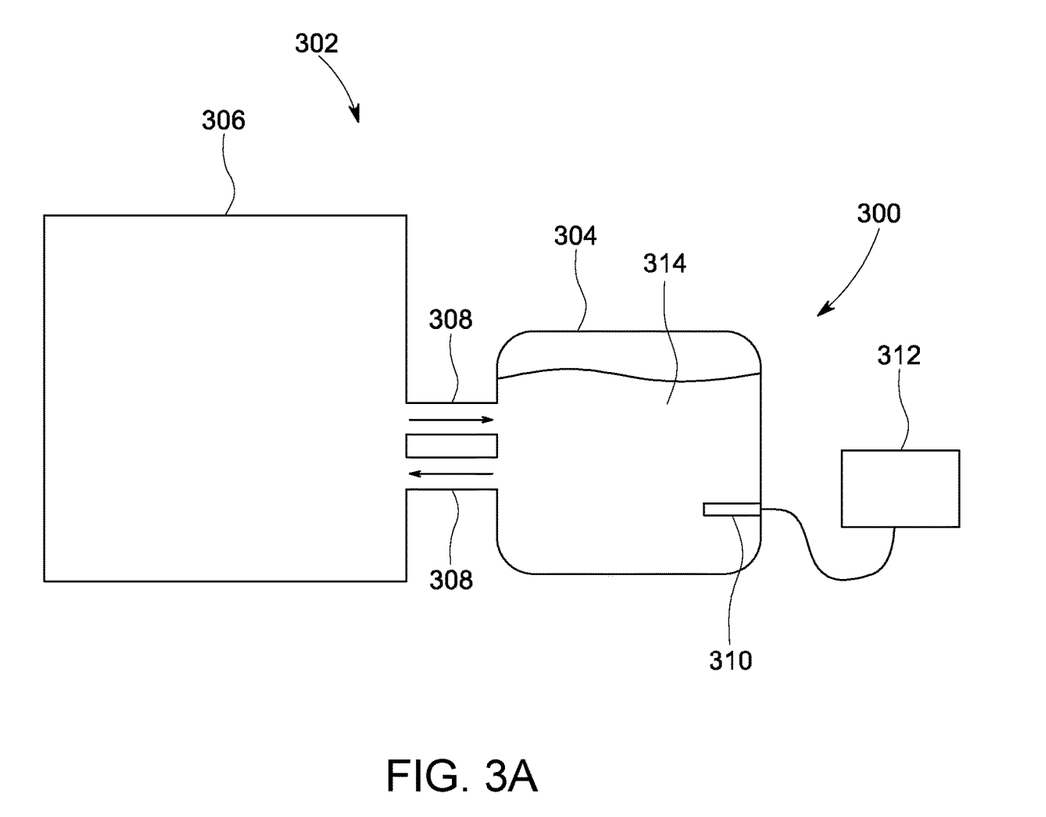
FIG. 3A is a schematic of an environment for monitoring lubrication using an oil sensor, according to some examples.

FIG. 3A is a schematic of an environment for monitoring lubrication using an oil sensor, according to some embodiments. FIG. 3A illustrates an environment 300 for monitoring the oil quality of a pump 302. The system 300 comprises a pump 302 having an oil reservoir 304. In the presently illustrated embodiment, the oil reservoir 304 is external to the main body 306 of the pump 302 while being in fluid connection with the pump 302 via hoses or pipes 308. This external reservoir 104 may be configured so that it can be retrofitted to an existing pump, or it may be designed as a fixed component of the pump.

In several embodiments, the pump 302 is a hydraulic fracturing (or "frac") pump, and the oil is for lubricant at the power end of the pump 302. Degradation of the oil can result in a reduction in performance of the pump 302 or wear of the components of the pump 302. To detect such degradation, an oil sensor 310 is positioned within the oil reservoir 304. Although this oil sensor 310 will be described in more detail below (with reference to FIGS. 3B and 3C), broadly, the oil sensor 110 may alternatively be used in a vehicle. That is, the oil sensor 310 may be configured for measuring various parameters of oil used in a car engine. In particular, the oil sensor 310 is of the type that is capable of measuring oil level, temperature, and the dielectric constant of the oil. These measurements are received, in the form of a voltage signal, by a processor 312 (in the form of a processing circuit, IC, PLD, SoC, microcontroller, server, distributed logic, or the like) that processes the signal and provides an indication of oil quality. This processing may include adjusting the measured dielectric constant based on the measured temperature.

A reduction in the dielectric constant of the oil may indicate that the oil has degraded. However, temperature also affects the dielectric constant of oil—e.g., as temperature increases, dielectric constant decrease. Hence, in order to provide an indication of oil quality, in some embodiments, the processor 312 removes variations in dielectric constant that are due to changes in temperature of the oil. This may be performed by adjusting the dielectric constant upwards in proportion to an increase in temperature, or downwards in proportion to a decrease in temperature (based on historical data of the relationship between dielectric constant and temperature).

As set forth above, environment 300 makes use of the oil sensor 310 that may be used in a vehicle or a pump. As is discussed above, automotive applications of such sensors differ significantly from the present application. One outcome of these significant differences is that in automotive applications level sensing (an integral component of such sensors) is valuable and feasible, whereas in the present application (e.g., with pumps) such sensing may be neither valuable or feasible.

Hence, due to the significantly different operating conditions (e.g., temperature, oil types, environment, etc.) between vehicles and pumps, such sensors were not considered suitable for use with pumps. However, it has been found that the present oil sensor 310, once the environment 300 is suitably adapted, can be used for measurement of oil quality in a frac pump 302. This adaptation includes positioning the oil sensor 310 so that, in operation, it is always fully immersed within oil 314 in the reservoir 304. The adaptation of the environment 300 also includes the provision of the oil reservoir 104 that is configured to ensure that the oil sensor 310 is able to remain full immersed within the oil 314 during operation of the frac pump 306. These adaptations are discussed further below.

Figure 3B:
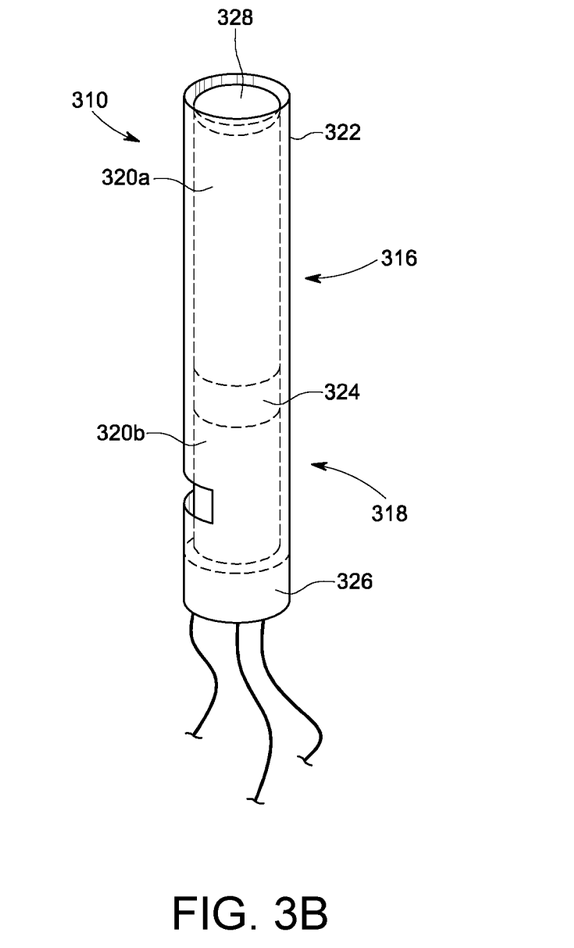
FIGS. 3B and 3C are perspective views of an oil sensor, according to some examples.
Figure 3C:
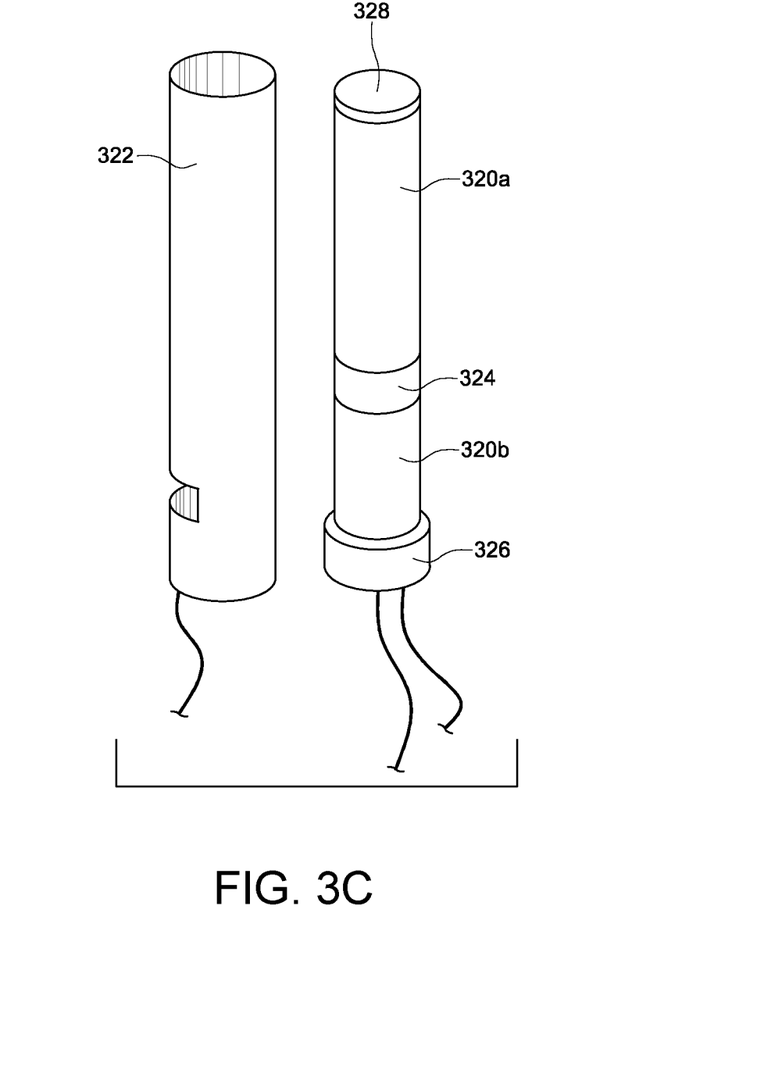

FIGS. 3B and 3C show the oil sensor 310 in more detail. In some embodiments, the sensor 310 includes first 316 and second 318 capacitive portions. Each capacitive portion 316, 318 includes a first capacitive element 320a, 320b and a second capacitive element 322, which is shared between the capacitive portions 316, 318.

The first capacitive elements 320a, 320b are generally tubular and formed of conductive material (e.g., metal). These are aligned along a common longitudinal axis and connected to one another by an insulating portion 324. Further insulating portions 326, 328 are disposed at either end of the connected first capacitive elements 320a, 320b. These insulating portions mean 324, 326, 328 that the first capacitive elements are not electrically connected to one another.

The second capacitive element 322 also has a tubular form and is formed of a conductive material. The first capacitive elements 320a, 320b of the capacitive portions 316, 318 are received within the hollow centre of the second capacitive element 322 so that the first 316 and second 318 capacitive elements are spaced and concentric with respect to one another. A distal end of the second capacitive element 322 is open to oil 314 within the oil reservoir 304, such that oil 314 can flow into the centre of the second capacitive element 322 and into the space formed between the second capacitive element 322 and the first capacitive elements 320a, 320b. An opening in a side of the second capacitive element 322 also allows oil 314 to pass into this space.

In operation, the oil forms the dielectric within each of the capacitive portions 316, 318. As set forth above, the oil sensor 310 is capable of detecting oil level and the dielectric constant of the oil 314. In the illustrated embodiment the first capacitive portion 316 is configured for measuring the level of oil 314 and the second capacitive portion 318 is configured for measuring the dielectric constant of the oil 314. The oil sensor 310 may be placed in a position where the oil level changes during operation. In particular, the positioning of the sensor 310 in its intended operation is such that the first capacitive portion 316 is only partially exposed to the oil 314, and as the oil level changes more or less of the first capacitive portion 316 becomes exposed. Under such conditions the electrical properties measured across the first capacitive portion 316 change, and these changes can be used to detect the level of the oil 314.

The second capacitive portion 318, which measured dielectric constant, works in a similar fashion. Changes in the electrical properties measured across the capacitive portion 318 are indicative of changes in dielectric constant of the oil filling the space between the first 320b and second 322 capacitive elements of the second capacitive portion 318.

Due to the structure of the oil sensor 310—for example, the capacitive portions 316, 318 sharing the second capacitive element 322—the level of the oil 314 can affect the measurement of the dielectric constant. This is acceptable where oil level changes happen gradually, but where there are significant and/or rapid changes in oil level (such as in a frac pump 306), the oil sensor 310 may provide inaccurate indications of oil quality.

As set forth above, in the present system 300 the oil sensor 310 is arranged such that it is always fully immersed in oil 314 during operation of the pump 306. In particular, the arrangement is such that the first capacitive portion 316, which measures the level of oil 314, is fully immersed. This is somewhat aided by the horizontal orientation of the sensor 310 in the oil reservoir 304. This full immersion is also a result of the design of the reservoir 304 (e.g., to ensure that it is always filled to a particular level under a range of operations of the pump 106) and the positioning of the oil sensor 310 within the reservoir 304.

By fully immersing the first capacitive portion 316, the oil sensor 310 always indicates that the oil 314 is at full level. Because oil level in the reservoir 304 is not relevant to operation of the frac pump 306 (although it may optionally be measured by a further sensor), this indication of oil level can be ignored. Notably, however, the consistent oil level ensures that the measurement of dielectric constant of the oil 314 is not affected by oil level changes. As such, the oil sensor 310 is able to provide reliable measurements of dielectric constant and these measurements do not need to be adjusted due to fluctuating oil level.

An exemplary work flow for determining the quality of oil in the reservoir of a pump (e.g., using the system as described above) is shown in FIG. 4. The work flow includes sensing dielectric constant and the temperature of the oil, using any of the disclosed oil sensors, as shown at 402-404. The dielectric constant and temperature values may further be utilized, but the oil level may not be. This is because, as in the environment 100 described above, the design of the reservoir 104 and oil sensor 110 is such that the oil sensor 110 (or at least the portion of the oil sensor 110 that measures oil level) is fully immersed during operation of the pump 102. That is, the oil level indicated by the oil sensor 110 is always constant, and is irrelevant to determining the oil quality, so is disregarded.

Figure 4:
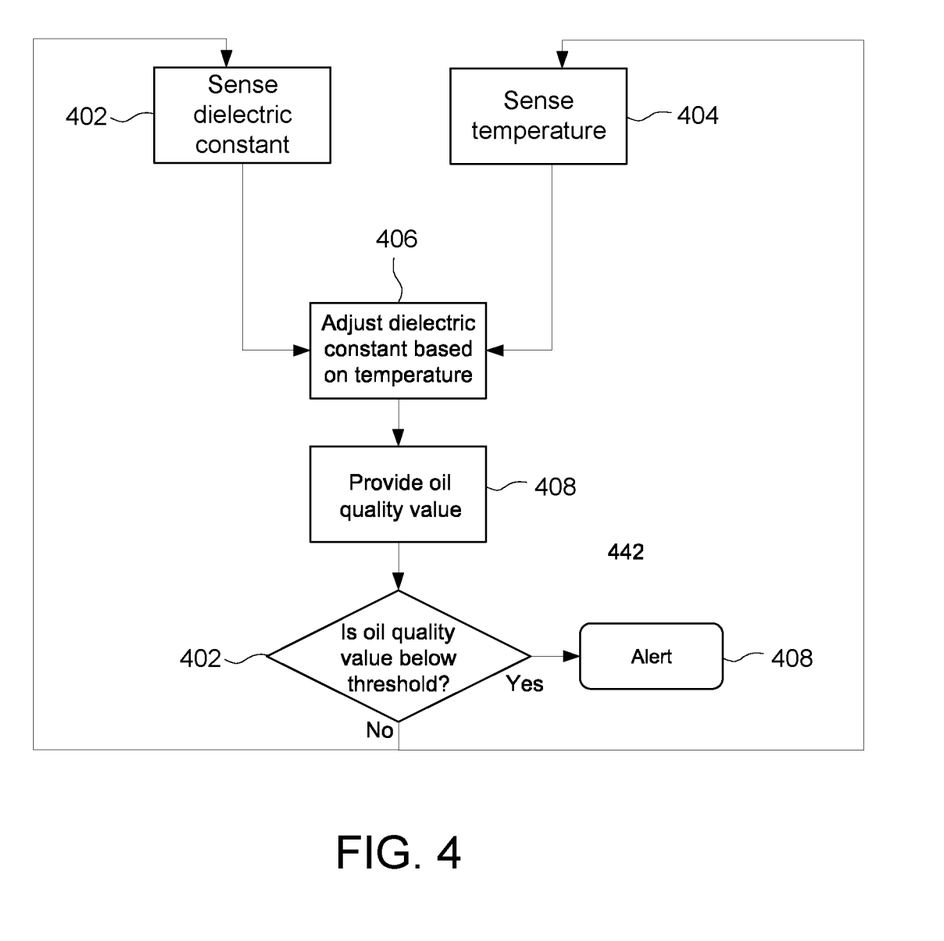
FIG. 4 is a flow chart showing a work flow for monitoring oil quality using an oil sensor, according to some examples.

As shown at 406, the sensed value of the dielectric constant is adjusted based on the sensed oil temperature. In particular, an increase in temperature results in an upward adjustment of the dielectric constant and vice-versa. Temperature increases cause drops in dielectric constant, so making this adjustment removes the effects of the temperature change from the measured or sensed value of dielectric constant. The adjustment 236 may be signalled by a processor, IC, PLD, SoC, microcontroller, or other processing unit.

The output of this adjustment is an indicator of the quality of the oil in the oil reservoir 238. This output is tested 240 (e.g., by the processor) against a threshold value. The threshold may be determined based on historical data for various installations, pump types, oil types, manufacturer, devices, or the like. In the illustrated embodiment, this threshold value is in the form of a lower limit. When the oil quality value falls below this predetermined threshold, it is indicative of the oil requiring replacement. An alert may be produced by the processor, which could be in the form of a visual or audible alert (e.g., to an operator) or an alert signal (e.g., to a pump controller), as shown at 408. On the other hand, if the oil quality value is above the threshold, the system may simply continue to monitor the oil quality, as shown by the return paths back to 402,404.

Variations and modifications may be made to the parts previously described without departing from the spirit or ambit of the disclosure.

For example, the sensor may be positioned in a sump of the frac pump, as long as it can be ensured that the positioning of the sensor in the sump is such that it will always be immersed in oil during operation of the pump.

Similarly, a cartridge arrangement may be provided at the oil sump of the frac pump (e.g., retrofitted). The cartridge may comprise the sensor and may be configured so as to ensure the oil sensor is maintained in an immersed or submerged state. The cartridge may also be removable in order to facilitate maintenance, replacement, or monitoring of the condition of the sensor. The cartridge may also be configured to ensure minimal flow rate of oil into the cartridge so as to minimise the rate of oil level changes. Again, this may help to ensure a generally constant level reading by the sensor.

Some examples are directed to an oil quality monitoring system. The system comprising: a pump comprising a lubrication circuit; a sensor comprising an electrode exposed to oil in the lubrication circuit, the electrode and the oil defining a capacitive portion that forms part of a resonant circuit of the sensor, the resonant circuit producing a signal, in use, that is indicative of oil quality in the lubrication circuit.

In some examples, the pump is a reciprocating pump.

In some examples, the pump is a frac pump.

In some examples, lubrication circuit supplies oil to components within a pump housing of the pump, and the sensor is mounted to a portion of the lubrication circuit that is external to the pump housing.

In some examples, the sensor is disposed with respect to the lubrication circuit such that the electrode is exposed to flowing oil in the lubrication circuit.

In some examples, the lubrication circuit comprises a sensor mounting portion comprising one or more sidewalls defining an internal cavity for receipt of oil, the sensor mounted in one of one or more sidewalls such that the electrode projects into the cavity.

In some examples, the sensor is releasably mounted in a mounting socket of the mounting portion, the mounting socket formed in a sidewall of the sensor mounting element.

In some examples, the lubrication circuit comprises an oil filter for filtering the oil, and the sensor is located so as to sense filtered oil between the oil filter and the pump housing.

Some examples include a processor for receiving the signal from the sensor, and processing the signal to determine a duty cycle value of the signal, the duty cycle being indicative of oil quality in the lubrication circuit.

In some examples, processor is further configured to adjust the duty cycle value to produce an adjusted value, the adjustment at least partially based on the temperature of the oil flow.

In some examples, the processor is further configured to adjust the duty cycle value to produce an adjusted value, the adjustment at least partially based on the type of oil in the oil flow.

In some examples, the processor is mounted to, or in proximity to, the pump.

In some examples, the processor is in wireless communication with a server, the server configured to receive and store the duty-cycle value or adjusted value from the processor.

In some examples, the server is accessible from a remote user device.

Some examples include an oil reservoir in fluid connection with the pump; and a sensor comprising: a first capacitive portion for measuring oil level; and a second capacitive portion for measuring dielectric constant of the oil.

In some examples, the first capacitive portion is arranged in the reservoir so as to remain substantially fully immersed in the oil during operation of the pump.

In some examples, the first and second capacitive portions each comprise a first capacitive element, and share a common second capacitive element spaced from the respective first capacitive elements.

In some examples, the second capacitive element is tubular, and each first capacitive element is arranged concentrically within the second capacitive element.

In some examples, the first capacitive elements are electrically insulated from one another.

In some examples, the sensor further comprises a temperature sensing portion for sensing the temperature of the oil.

In some examples, the processor adapted to adjust the sensed dielectric constant based on the sensed temperature of the oil.

In some examples, the oil reservoir is fluidly connected to a power end sump of the pump.

In some examples, the oil reservoir is configured to maintain an oil level in the oil reservoir that is sufficient to substantially immerse the sensor in the oil during operation of the pump.

In some examples, the sensor is an automotive sensor.

In some examples, the pump is a positive displacement pump.

Some examples are directed to a method of determining the quality of oil in the reservoir of a pump. The method includes: providing a sensor capable of sensing: the dielectric constant of oil, and oil level based on the degree of exposure of the sensor to the oil; exposing the sensor to a substantially constant oil level; and determining quality of the oil based on the sensed dielectric constant of the oil.

Some examples include fully immersing an oil level sensing portion of the sensor in the oil.

In some examples, the temperature of the oil is sensed.

In some examples, the sensed dielectric constant is adjusted based on the sensed oil temperature in order to determine the quality of the oil.

Some examples are directed to a method of retrofitting a frac pump with an oil quality detection system. The method includes mounting a sensor in an oil reservoir of the frac pump. The sensor includes a first capacitive portion for measuring oil level; and a second capacitive portion for measuring dielectric constant of the oil.

In some examples, the external reservoir is fluidly connected to the frac pump, and the sensor being mounted in the external reservoir.

In some examples, the sensor is mounted in the oil reservoir such that the first capacitive portion remains immersed in oil during operation of the frac pump.

While the aspects of the disclosure have been described in terms of various examples with their associated operations, a person skilled in the art would appreciate that a combination of operations from any number of different examples is also within scope of the aspects of the disclosure.

Some portions of the disclosed examples and embodiments may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein. In examples involving a general-purpose computer, aspects of the disclosure transform the general-purpose computer into a special-purpose computing device when configured to execute the instructions described herein.

By way of example and not limitation, computer readable media comprise computer storage media devices and communication media. Computer storage media devices include volatile and nonvolatile, removable and non-removable memory implemented in any method or technology for storage of information such as computer readable instructions, data structures, program modules, or the like. Computer storage media devices are tangible and mutually exclusive to communication media. Computer storage media devices are implemented in hardware and exclude carrier waves and propagated signals. Computer storage media devices for purposes of this disclosure are not signals per se. Example computer storage media devices include hard disks, flash drives, solid-state memory, phase change random-access memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that can be used to store information for access by a computing device. In contrast, communication media typically embody computer readable instructions, data structures, program modules, or the like in a modulated data signal such as a carrier wave or other transport mechanism and include any information delivery media.

The examples illustrated and described herein, as well as examples not specifically described herein but within the scope of aspects of the disclosure, constitute exemplary means for monitoring oil parameters in lubricants of a frac pump. For example, the elements described in FIGS. 1-3C, when used to perform the operations illustrated in FIG. 4, constitute exemplary means for monitoring oil and alerting an operator when said oil parameters exceed various threshold limits.

The order of execution or performance of the operations in examples of the disclosure illustrated and described herein is not essential, and may be performed in different sequential manners in various examples. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of" The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The invention claimed is:

1. An oil quality monitoring A system for monitoring oil quality in a pump, the system comprising:
   a lubrication circuit coupled to the pump; and
   an oil sensor comprising:
      a first capacitive portion for measuring a level of the oil; and
      a second capacitive portion for measuring a dielectric constant of the oil,
         wherein the first and second capacitive portions each include a first capacitive element and share a common second capacitive element spaced from the respective first capacitive elements,
         wherein the second capacitive element is tubular, and
         wherein each first capacitive element is arranged concentrically within the second capacitive element.

2. The system of claim 1, wherein the pump is a reciprocating pump.

3. The system of claim 1, wherein the pump is a frac pump.

4. The system of claim 3, wherein the lubrication circuit supplies oil to components within a pump housing of the pump, and the oil sensor is mounted to a portion of the lubrication circuit that is external to the pump housing.

5. The system of claim 1, wherein the lubrication circuit comprises a sensor mounting portion comprising one or more sidewalls defining an internal cavity for receipt of oil, and wherein the oil sensor is mounted in a first sidewall, of the one or more sidewalls such that the oil sensor projects into the internal cavity.

6. The system of claim 5, wherein the oil sensor is releasably mounted in a mounting socket of the sensor mounting portion, and wherein the mounting socket is formed in the first sidewall of the mounting portion.

7. The system of claim 1, further comprising:
   a processor for receiving the signal from the oil sensor, and processing the signal to determine a duty cycle value of the signal, the duty cycle being indicative of oil quality in the lubrication circuit.

8. The system of claim 7, wherein the processor is further configured to adjust the duty cycle value to produce an adjusted value, the adjustment at least partially based on a temperature of the oil .

9. The system of claim 7, wherein the processor is further configured to adjust the duty cycle value to produce an adjusted value, the adjustment at least partially based on a type of oil in the lubrication circuit.

10. The system of claim 7 wherein the processor is mounted to, or in proximity to, the pump.

11. A system for monitoring an oil quality of a pump, the system comprising:
   an oil reservoir in fluid connection with the pump; and
   a sensor comprising:
      a first capacitive portion for measuring oil level; and
      a second capacitive portion for measuring a dielectric constant of the oil,
         wherein the first and second capacitive portions each include a first capacitive element and share a common second capacitive element spaced from the respective first capacitive elements,
         wherein the second capacitive element is tubular, and
         wherein each first capacitive element is arranged concentrically within the second capacitive element.

12. The system of claim 11 wherein the first capacitive portion is arranged in the oil reservoir so as to remain substantially fully immersed in the oil during operation of the pump.

13. The system of claim 11 wherein two of the first capacitive elements are electrically insulated from one another.

14. The system of claim 11 wherein the sensor further comprises a temperature sensing portion for sensing the temperature of the oil.

15. A method of determining a quality of oil in a reservoir of a pump, the method comprising:
   providing a sensor including:
      a first capacitive portion for measuring a level of the oil based on a degree of exposure of the sensor to the oil; and
      a second capacitive portion for measuring a dielectric constant of the oil,
         wherein the first and second capacitive portions each include a first capacitive element and share a common second capacitive element spaced from the respective first capacitive elements,
         wherein the second capacitive element is tubular, and
         wherein each first capacitive element is arranged concentrically within the second capacitive element;
   exposing the sensor to a substantially constant oil level; and
   determining the quality of the oil based on the sensed dielectric constant of the oil.

16. The method of claim 15 further comprising fully immersing an oil level sensing portion of the sensor in the oil.

17. The method of claim 15 further comprising sensing a temperature of the oil.

18. The method of claim 15 wherein the sensed dielectric constant is adjusted based on a sensed oil temperature in order to determine the quality of the oil.

* * * * *